(12) United States Patent
Miller et al.

(10) Patent No.: US 8,343,215 B2
(45) Date of Patent: Jan. 1, 2013

(54) SYSTEM AND METHOD FOR INCREASING THE DEPTH OF FOCUS OF THE HUMAN EYE

(75) Inventors: David Miller, Brookline, MA (US); Ernesto Blanco, Belmont, MA (US)

(73) Assignee: AcuFocus, Inc., Irvine, CA (US)

( * ) Notice: Subject to any disclaimer, the term of this patent is extended or adjusted under 35 U.S.C. 154(b) by 531 days.

(21) Appl. No.: 12/182,056

(22) Filed: Jul. 29, 2008

(65) Prior Publication Data
US 2009/0021692 A1  Jan. 22, 2009

Related U.S. Application Data

(62) Division of application No. 11/284,791, filed on Nov. 22, 2005, now Pat. No. 7,404,638, which is a division of application No. 10/729,200, filed on Dec. 5, 2003, now Pat. No. 6,966,648, which is a division of application No. 10/384,957, filed on Mar. 10, 2003, now Pat. No. 6,874,886, which is a division of application No. 09/516,258, filed on Feb. 29, 2000, now Pat. No. 6,554,424, application No. 12/182,056, which is a division of application No. 09/516,258, filed on Feb. 29, 2000, now Pat. No. 6,554,424.

(60) Provisional application No. 60/122,001, filed on Mar. 1, 1999, provisional application No. 60/124,345, filed on Mar. 15, 1999, provisional application No. 60/138,110, filed on Jun. 7, 1999.

(51) Int. Cl.
*A61F 2/14* (2006.01)

(52) U.S. Cl. ...................... 623/5.11; 623/5.12

(58) Field of Classification Search .................. None
See application file for complete search history.

(56) References Cited

U.S. PATENT DOCUMENTS
564,518 A  7/1896  Heilborn
(Continued)

FOREIGN PATENT DOCUMENTS
EP  0 457 553 A2  11/1991
(Continued)

OTHER PUBLICATIONS

Accommodation and Presbyopia. Croft et al. pp. 33-46.
(Continued)

*Primary Examiner* — David H Willse
*Assistant Examiner* — Javier Blanco
(74) *Attorney, Agent, or Firm* — Knobbe Martens Olson & Bear LLP

(57) ABSTRACT

A method and apparatus for increasing the depth of focus of the human eye is comprised of a lens body, an optic in the lens body configured to produce light interference, and a pinhole-like optical aperture substantially in the center of the optic. The optic may be configured to produce light scattering or composed of a light reflective material. Alternatively, the optic may increase the depth of focus via a combination of light interference, light scattering, light reflection and/or light absorption. The optic may also be configured as a series of concentric circles, a weave, a pattern of particles, or a pattern of curvatures. One method involves screening a patient for an ophthalmic lens using a pinhole screening device in the lens to increase the patient's depth of focus. Another method comprises surgically implanting a mask in the patient's eye to increase the depth of focus.

24 Claims, 7 Drawing Sheets

U.S. PATENT DOCUMENTS

| | | |
|---|---|---|
| 1,206,132 A | 11/1916 | Otte |
| 1,959,915 A | 5/1934 | Guthrie |
| 2,129,305 A | 9/1938 | Feinbloom |
| 2,714,721 A | 8/1955 | Stone, Jr. |
| 3,034,403 A | 4/1959 | Neefe |
| 3,270,099 A | 8/1966 | Camp |
| 3,339,997 A | 9/1967 | Wesley |
| 3,458,870 A | 8/1969 | Stone, Jr. |
| 3,507,566 A | 4/1970 | Knapp |
| 3,578,850 A | 5/1971 | Grant |
| 3,600,098 A | 8/1971 | Mohrman |
| 3,726,587 A | 4/1973 | Kendall |
| 3,794,414 A | 2/1974 | Wesley |
| 3,852,032 A | 12/1974 | Urbach |
| 3,982,541 A | 9/1976 | L'Esperance, Jr. |
| 4,010,496 A | 3/1977 | Neefe |
| 4,073,015 A | 2/1978 | Peyman |
| 4,099,529 A | 7/1978 | Peyman |
| 4,138,191 A | 2/1979 | Peyman |
| 4,191,195 A | 3/1980 | Miller |
| 4,272,191 A | 6/1981 | Bergkvist |
| 4,298,004 A | 11/1981 | Schachar et al. |
| 4,312,575 A | 1/1982 | Peyman et al. |
| 4,367,949 A | 1/1983 | Lavering |
| 4,402,681 A | 9/1983 | Haas et al. |
| 4,450,593 A | 5/1984 | Poler |
| 4,452,235 A | 6/1984 | Reynolds |
| 4,485,499 A | 12/1984 | Castleman |
| 4,528,311 A | 7/1985 | Beard et al. |
| 4,536,240 A | 8/1985 | Winn |
| 4,547,914 A | 10/1985 | Castleman |
| 4,547,915 A | 10/1985 | Castleman |
| 4,575,915 A | 3/1986 | Clark et al. |
| 4,576,453 A | 3/1986 | Borowsky |
| 4,607,617 A | 8/1986 | Choyce |
| 4,612,012 A | 9/1986 | White |
| 4,615,702 A | 10/1986 | Koziol et al. |
| 4,617,023 A | 10/1986 | Peyman |
| 4,624,669 A | 11/1986 | Grendahl |
| 4,633,866 A | 1/1987 | Peyman et al. |
| 4,636,049 A | 1/1987 | Blaker |
| 4,636,211 A | 1/1987 | Nielsen et al. |
| 4,636,212 A | 1/1987 | Posin et al. |
| 4,637,697 A | 1/1987 | Freeman |
| 4,639,105 A | 1/1987 | Neefe |
| 4,641,934 A | 2/1987 | Freeman |
| 4,642,112 A | 2/1987 | Freeman |
| 4,646,720 A | 3/1987 | Peyman et al. |
| 4,655,774 A | 4/1987 | Choyce |
| 4,662,370 A | 5/1987 | Hoffman et al. |
| 4,665,913 A | 5/1987 | L'Esperance, Jr. |
| 4,666,446 A | 5/1987 | Koziol et al. |
| 4,669,466 A | 6/1987 | L'Esperance, Jr. |
| 4,669,834 A | 6/1987 | Richter |
| 4,674,503 A | 6/1987 | Peyman et al. |
| 4,676,790 A | 6/1987 | Kern |
| 4,676,791 A | 6/1987 | LeMaster et al. |
| 4,685,922 A | 8/1987 | Peyman |
| 4,701,038 A | 10/1987 | Neefe |
| 4,702,865 A | 10/1987 | Koziol et al. |
| 4,704,016 A | 11/1987 | de Carle |
| 4,710,003 A | 12/1987 | Masuda et al. |
| 4,713,446 A | 12/1987 | DeVore et al. |
| 4,715,858 A | 12/1987 | Lindstrom |
| 4,718,418 A | 1/1988 | L'Esperance |
| 4,729,372 A | 3/1988 | L'Esperance, Jr. |
| 4,729,373 A | 3/1988 | Peyman |
| 4,744,360 A | 5/1988 | Bath |
| 4,753,654 A | 6/1988 | Posin et al. |
| 4,779,973 A | 10/1988 | Miller et al. |
| 4,785,796 A | 11/1988 | Mattson |
| 4,799,784 A | 1/1989 | Safir |
| 4,799,931 A | 1/1989 | Lindstrom |
| 4,807,623 A | 2/1989 | Lieberman |
| 4,808,181 A | 2/1989 | Kelman |
| 4,813,955 A | 3/1989 | Achatz et al. |
| 4,814,050 A | 3/1989 | McGraw et al. |
| 4,838,266 A | 6/1989 | Koziol et al. |
| 4,840,175 A | 6/1989 | Peyman |
| 4,842,599 A | 6/1989 | Bronstein |
| 4,851,003 A * | 7/1989 | Lindstrom .................. 623/5.13 |
| 4,863,466 A | 9/1989 | Schlegel |
| 4,865,601 A | 9/1989 | Caldwell et al. |
| 4,869,587 A | 9/1989 | Breger |
| 4,878,910 A | 11/1989 | Koziol et al. |
| 4,881,954 A | 11/1989 | Bikson et al. |
| 4,890,913 A | 1/1990 | De Carle |
| 4,891,043 A | 1/1990 | Zeimer et al. |
| 4,898,461 A | 2/1990 | Portney |
| 4,903,695 A | 2/1990 | Warner et al. |
| 4,923,297 A | 5/1990 | Arndt |
| 4,932,970 A | 6/1990 | Portney |
| 4,955,904 A | 9/1990 | Atebara et al. |
| 4,958,922 A | 9/1990 | Binh et al. |
| 4,961,744 A | 10/1990 | Kilmer et al. |
| 4,965,545 A | 10/1990 | Johnson |
| 4,971,432 A | 11/1990 | Koeniger |
| 4,976,732 A | 12/1990 | Vorosmarthy |
| 4,983,181 A | 1/1991 | Civerchia |
| 4,985,559 A | 1/1991 | Goldberg et al. |
| 4,990,165 A | 2/1991 | Bikson et al. |
| 4,994,058 A | 2/1991 | Raven et al. |
| 4,994,080 A | 2/1991 | Shepard |
| 4,997,268 A | 3/1991 | Dauvergne |
| 5,002,571 A | 3/1991 | O'Donnell, Jr. |
| 5,013,319 A | 5/1991 | Davis |
| 5,019,097 A | 5/1991 | Knight et al. |
| 5,026,393 A | 6/1991 | Mackool |
| 5,030,230 A | 7/1991 | White |
| 5,041,133 A | 8/1991 | Sayano et al. |
| 5,061,914 A | 10/1991 | Busch et al. |
| 5,063,942 A | 11/1991 | Kilmer et al. |
| 5,067,961 A | 11/1991 | Kelman et al. |
| 5,076,684 A | 12/1991 | Simpson et al. |
| 5,089,022 A | 2/1992 | Koester et al. |
| 5,089,024 A | 2/1992 | Christie et al. |
| 5,098,443 A | 3/1992 | Parel et al. |
| 5,098,444 A | 3/1992 | Feaster |
| 5,104,957 A | 4/1992 | Kelman et al. |
| 5,108,169 A | 4/1992 | Mandell |
| 5,108,428 A | 4/1992 | Capecchi et al. |
| 5,112,350 A | 5/1992 | Civerchia et al. |
| 5,116,111 A | 5/1992 | Simpson et al. |
| 5,119,555 A | 6/1992 | Johnson |
| 5,120,120 A | 6/1992 | Cohen |
| 5,123,921 A | 6/1992 | Werblin et al. |
| 5,133,745 A | 7/1992 | Falcetta et al. |
| 5,149,331 A | 9/1992 | Ferdman et al. |
| 5,152,789 A | 10/1992 | Willis |
| 5,160,463 A | 11/1992 | Evans et al. |
| 5,165,897 A | 11/1992 | Johnson |
| 5,166,712 A | 11/1992 | Portney |
| 5,171,318 A * | 12/1992 | Gibson et al. ................. 623/5.16 |
| 5,185,152 A | 2/1993 | Peyman |
| 5,192,316 A * | 3/1993 | Ting .......................... 623/5.16 |
| 5,192,318 A | 3/1993 | Schneider et al. |
| 5,196,026 A | 3/1993 | Barrett et al. |
| 5,215,104 A | 6/1993 | Steinert |
| 5,219,844 A | 6/1993 | Peyman et al. |
| 5,225,858 A | 7/1993 | Portney |
| 5,239,066 A | 8/1993 | Falkow et al. |
| 5,245,367 A | 9/1993 | Miller et al. |
| 5,245,738 A | 9/1993 | Johnson |
| 5,258,412 A | 11/1993 | Peyman et al. |
| 5,260,727 A | 11/1993 | Oksman et al. |
| 5,261,997 A | 11/1993 | Inselmann |
| 5,269,812 A | 12/1993 | White |
| 5,270,744 A | 12/1993 | Portney |
| 5,274,404 A | 12/1993 | Michael |
| 5,292,514 A | 3/1994 | Capecchi et al. |
| 5,296,881 A | 3/1994 | Freeman |
| 5,300,116 A | 4/1994 | Chirila et al. |
| 5,300,118 A | 4/1994 | Silvestrini et al. |
| 5,302,978 A | 4/1994 | Evans et al. |
| 5,310,654 A | 5/1994 | Isberg et al. |
| 5,312,393 A | 5/1994 | Mastel |
| 5,314,439 A | 5/1994 | Sugita |

| Patent No. | Date | Inventor |
|---|---|---|
| 5,314,961 A | 5/1994 | Anton et al. |
| 5,315,344 A | 5/1994 | Clark et al. |
| 5,318,044 A | 6/1994 | Kilmer et al. |
| 5,318,047 A | 6/1994 | Davenport et al. |
| 5,323,788 A | 6/1994 | Silvestrini et al. |
| 5,325,880 A | 7/1994 | Johnson et al. |
| 5,336,261 A | 8/1994 | Barret et al. |
| 5,346,689 A | 9/1994 | Peyman et al. |
| 5,354,331 A | 10/1994 | Schachar |
| 5,366,499 A | 11/1994 | Py |
| 5,368,604 A | 11/1994 | Kilmer et al. |
| 5,374,272 A | 12/1994 | Arpa et al. |
| D354,566 S | 1/1995 | Donahoo |
| 5,391,201 A | 2/1995 | Barret et al. |
| 5,401,508 A | 3/1995 | Manesis |
| 5,403,335 A | 4/1995 | Loomas et al. |
| 5,405,384 A | 4/1995 | Silvestrini |
| 5,422,424 A | 6/1995 | Selsted et al. |
| 5,433,745 A | 7/1995 | Graham et al. |
| 5,434,630 A | 7/1995 | Bransome |
| 5,437,274 A | 8/1995 | Khoobehi et al. |
| 5,458,819 A | 10/1995 | Chirila et al. |
| 5,474,548 A | 12/1995 | Knopp et al. |
| 5,476,515 A | 12/1995 | Kelman et al. |
| 5,480,427 A | 1/1996 | Kelman et al. |
| 5,489,300 A | 2/1996 | Capecchi et al. |
| 5,496,339 A | 3/1996 | Koepnick |
| 5,505,723 A | 4/1996 | Muller |
| 5,507,740 A | 4/1996 | O'Donnel, Jr. |
| 5,516,522 A | 5/1996 | Peyman et al. |
| 5,522,888 A | 6/1996 | Civerchia |
| 5,526,178 A | 6/1996 | Goldstein et al. |
| 5,527,356 A | 6/1996 | Peyman et al. |
| 5,547,473 A | 8/1996 | Peyman |
| 5,567,365 A | 10/1996 | Weinschenk, III et al. |
| 5,571,177 A | 11/1996 | Deacon et al. |
| 5,579,063 A | 11/1996 | Magnante et al. |
| RE35,421 E | 1/1997 | Ruiz et al. |
| 5,599,537 A | 2/1997 | Miller, III et al. |
| 5,605,938 A | 2/1997 | Roufa et al. |
| 5,608,471 A | 3/1997 | Miller |
| 5,610,719 A | 3/1997 | Allen et al. |
| 5,628,794 A | 5/1997 | Lindstrom |
| 5,628,795 A | 5/1997 | Langerman |
| 5,628,798 A | 5/1997 | Eggleston et al. |
| 5,631,243 A | 5/1997 | Kelman et al. |
| 5,632,773 A | 5/1997 | Graham et al. |
| 5,662,706 A | 9/1997 | Legerton et al. |
| 5,662,908 A | 9/1997 | Falkow et al. |
| 5,672,885 A | 9/1997 | Allen et al. |
| 5,674,724 A | 10/1997 | Miller, III et al. |
| 5,674,736 A | 10/1997 | Miller, III et al. |
| 5,693,092 A | 12/1997 | Silvestrini et al. |
| 5,695,983 A | 12/1997 | Miller et al. |
| 5,697,923 A | 12/1997 | Poler |
| 5,697,973 A | 12/1997 | Peyman et al. |
| 5,702,440 A | 12/1997 | Portney |
| 5,713,844 A | 2/1998 | Peyman |
| 5,713,957 A | 2/1998 | Steele et al. |
| 5,719,656 A | 2/1998 | Bowling |
| 5,720,894 A | 2/1998 | Neev et al. |
| 5,722,971 A | 3/1998 | Peyman |
| 5,731,196 A | 3/1998 | Miller, III et al. |
| 5,731,862 A | 3/1998 | Winkler |
| 5,733,760 A | 3/1998 | Lu et al. |
| 5,752,967 A | 5/1998 | Kritzinger et al. |
| 5,757,458 A | 5/1998 | Miller et al. |
| 5,771,088 A | 6/1998 | Perrott |
| 5,771,742 A | 6/1998 | Bokaie et al. |
| 5,774,202 A | 6/1998 | Abraham et al. |
| 5,782,911 A | 7/1998 | Herrick |
| 5,786,883 A | 7/1998 | Miller et al. |
| 5,800,533 A | 9/1998 | Eggleston et al. |
| 5,806,530 A | 9/1998 | Herrick |
| 5,814,680 A | 9/1998 | Imafuku et al. |
| 5,836,313 A | 11/1998 | Perez et al. |
| 5,840,848 A | 11/1998 | Sturrock et al. |
| 5,855,605 A | 1/1999 | Herrick |
| 5,858,980 A | 1/1999 | Weiner et al. |
| 5,861,486 A | 1/1999 | Devore et al. |
| 5,863,537 A | 1/1999 | Dalie et al. |
| 5,864,128 A | 1/1999 | Plesko |
| 5,864,378 A | 1/1999 | Portney |
| 5,874,537 A | 2/1999 | Kelman et al. |
| 5,903,099 A | 5/1999 | Johnson et al. |
| 5,905,561 A | 5/1999 | Lee et al. |
| 5,919,185 A * | 7/1999 | Peyman ............... 623/5.11 |
| 5,929,968 A | 7/1999 | Cotie et al. |
| 5,946,748 A | 9/1999 | Wang |
| 5,960,812 A | 10/1999 | Johnson |
| 5,964,748 A | 10/1999 | Peyman |
| 5,964,776 A | 10/1999 | Peyman |
| 5,965,330 A | 10/1999 | Evans et al. |
| 5,980,040 A | 11/1999 | Xu et al. |
| 5,997,559 A | 12/1999 | Ziemer |
| 6,010,901 A | 1/2000 | Miller, III et al. |
| 6,024,447 A | 2/2000 | Portney |
| 6,036,957 A | 3/2000 | Weiner et al. |
| 6,050,999 A | 4/2000 | Paraschac et al. |
| 6,063,073 A | 5/2000 | Peyman |
| 6,083,236 A | 7/2000 | Feingold |
| 6,086,204 A | 7/2000 | Magnante |
| 6,090,141 A | 7/2000 | Lindstrom |
| 6,096,077 A | 8/2000 | Callahan et al. |
| 6,102,946 A | 8/2000 | Nigam |
| 6,106,552 A | 8/2000 | Lacombe et al. |
| 6,126,286 A | 10/2000 | Portney |
| 6,161,544 A | 12/2000 | DeVore et al. |
| 6,164,282 A | 12/2000 | Gwon et al. |
| 6,165,189 A | 12/2000 | Ziemer |
| 6,171,336 B1 | 1/2001 | Sawusch |
| 6,176,878 B1 | 1/2001 | Gwon et al. |
| 6,183,498 B1 | 2/2001 | Devore et al. |
| 6,197,019 B1 | 3/2001 | Peyman |
| 6,197,057 B1 | 3/2001 | Peyman et al. |
| 6,197,934 B1 | 3/2001 | DeVore et al. |
| 6,203,538 B1 | 3/2001 | Peyman |
| 6,204,365 B1 | 3/2001 | Devore et al. |
| 6,210,005 B1 | 4/2001 | Portney |
| 6,217,571 B1 | 4/2001 | Peyman |
| 6,217,596 B1 | 4/2001 | Farah |
| 6,221,067 B1 | 4/2001 | Peyman |
| 6,221,105 B1 | 4/2001 | Portney |
| 6,228,114 B1 | 5/2001 | Lee |
| 6,251,118 B1 | 6/2001 | Proudfoot et al. |
| 6,277,146 B1 | 8/2001 | Peyman et al. |
| 6,280,470 B1 | 8/2001 | Peyman |
| 6,280,471 B1 | 8/2001 | Peyman |
| 6,283,595 B1 | 9/2001 | Breger |
| 6,335,006 B1 | 1/2002 | Miller |
| 6,357,875 B1 | 3/2002 | Herrick |
| 6,358,280 B1 | 3/2002 | Herrick |
| 6,361,560 B1 | 3/2002 | Nigam |
| 6,387,379 B1 | 5/2002 | Goldberg et al. |
| 6,391,055 B1 | 5/2002 | Ikada et al. |
| 6,403,947 B1 | 6/2002 | Hoyt et al. |
| 6,406,494 B1 | 6/2002 | Laguette et al. |
| 6,416,179 B1 | 7/2002 | Lieberman et al. |
| 6,423,093 B1 * | 7/2002 | Hicks et al. ............... 623/5.11 |
| 6,436,092 B1 | 8/2002 | Peyman |
| 6,457,826 B1 | 10/2002 | Lett |
| 6,458,141 B1 | 10/2002 | Peyman |
| 6,470,108 B1 | 10/2002 | Johnson |
| 6,488,707 B1 | 12/2002 | Callahan et al. |
| 6,494,910 B1 | 12/2002 | Ganem et al. |
| 6,497,700 B1 | 12/2002 | LaHaye |
| 6,503,276 B2 | 1/2003 | Lang et al. |
| 6,527,389 B2 | 3/2003 | Portney |
| 6,533,905 B2 | 3/2003 | Johnson et al. |
| 6,536,899 B1 | 3/2003 | Fiala |
| 6,551,307 B2 | 4/2003 | Peyman |
| 6,554,424 B1 | 4/2003 | Miller et al. |
| 6,555,103 B2 | 4/2003 | Leukel et al. |
| 6,569,199 B1 | 5/2003 | Dotan et al. |
| 6,581,993 B2 | 6/2003 | Nigam |
| RE38,193 E | 7/2003 | Bowling |
| 6,588,022 B1 | 7/2003 | Anders et al. |
| 6,588,902 B2 | 7/2003 | Isogai |

| Patent/Pub No. | Date | Name |
|---|---|---|
| 6,589,280 B1 | 7/2003 | Koziol |
| 6,592,621 B1 | 7/2003 | Domino |
| 6,599,305 B1 | 7/2003 | Feingold |
| 6,607,556 B1 | 8/2003 | Nigam |
| 6,613,088 B1 | 9/2003 | Babizhayev |
| 6,614,570 B2 | 9/2003 | Johnson et al. |
| 6,620,634 B2 | 9/2003 | Johnson et al. |
| 6,623,497 B1 | 9/2003 | Feingold |
| 6,623,522 B2 | 9/2003 | Nigam |
| 6,624,730 B2 | 9/2003 | Johnson et al. |
| 6,626,941 B2 | 9/2003 | Nigam |
| 6,632,244 B1 | 10/2003 | Nigam |
| 6,663,668 B1 | 12/2003 | Chaouk et al. |
| 6,669,795 B2 | 12/2003 | Johnson et al. |
| 6,673,112 B2 | 1/2004 | Nigam |
| 6,729,599 B2 | 5/2004 | Johnson |
| 6,740,116 B2 | 5/2004 | Morcher |
| 6,742,761 B2 | 6/2004 | Johnson et al. |
| 6,746,890 B2 | 6/2004 | Gupta et al. |
| 6,755,858 B1 | 6/2004 | White |
| 6,786,926 B2 | 9/2004 | Peyman |
| 6,790,298 B2 | 9/2004 | Johnson et al. |
| 6,811,256 B1 | 11/2004 | Becherer et al. |
| 6,849,090 B2 | 2/2005 | Nigam |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,976,997 B2 | 12/2005 | Noolandi et al. |
| 7,025,455 B2 | 4/2006 | Roffman |
| 7,207,998 B2 | 4/2007 | Feingold |
| 7,364,674 B1 | 4/2008 | Hoover |
| 7,404,637 B2 | 7/2008 | Miller et al. |
| 7,404,638 B2 | 7/2008 | Miller et al. |
| 7,491,350 B2 | 2/2009 | Silvestrini |
| 7,628,810 B2 | 12/2009 | Christie et al. |
| 7,645,291 B2 | 1/2010 | Ross et al. |
| 7,828,844 B2 | 11/2010 | Marmo et al. |
| 2001/0004702 A1 | 6/2001 | Peyman |
| 2001/0027314 A1 | 10/2001 | Peyman |
| 2001/0034516 A1 | 10/2001 | Peyman |
| 2001/0047203 A1 | 11/2001 | Dalton et al. |
| 2001/0050750 A1 | 12/2001 | Breger |
| 2002/0010510 A1 | 1/2002 | Silvestrini |
| 2002/0028330 A1 | 3/2002 | Patel et al. |
| 2002/0055753 A1 | 5/2002 | Silvestrini |
| 2002/0057148 A1 | 5/2002 | Johnson et al. |
| 2002/0075447 A1 | 6/2002 | Andino et al. |
| 2002/0107337 A1 | 8/2002 | Rosenzweig et al. |
| 2002/0107566 A1 | 8/2002 | Nigam |
| 2002/0111677 A1 | 8/2002 | Nigam |
| 2002/0128710 A1 | 9/2002 | Eggleston |
| 2002/0167640 A1 | 11/2002 | Francis et al. |
| 2002/0188351 A1 | 12/2002 | Laguette |
| 2002/0196409 A1 | 12/2002 | Jani |
| 2003/0002994 A1 | 1/2003 | Johnson et al. |
| 2003/0007122 A1 | 1/2003 | Streibig |
| 2003/0014042 A1* | 1/2003 | Juhasz et al. ............ 606/5 |
| 2003/0014107 A1 | 1/2003 | Reynard |
| 2003/0033013 A1 | 2/2003 | Callahan et al. |
| 2003/0045930 A1 | 3/2003 | Nguyen |
| 2003/0055497 A1 | 3/2003 | Hicks et al. |
| 2003/0071893 A1 | 4/2003 | Miller et al. |
| 2003/0078655 A1 | 4/2003 | Callahan et al. |
| 2003/0088313 A1 | 5/2003 | Nigam |
| 2003/0093083 A1 | 5/2003 | Peyman |
| 2003/0105521 A1 | 6/2003 | Perez |
| 2003/0127318 A1 | 7/2003 | Johnson et al. |
| 2003/0220653 A1 | 11/2003 | Perez |
| 2004/0014253 A1 | 1/2004 | Gupta et al. |
| 2004/0015234 A1 | 1/2004 | Peyman |
| 2004/0019379 A1 | 1/2004 | Glick et al. |
| 2004/0047014 A1 | 3/2004 | Parker et al. |
| 2004/0068317 A1 | 4/2004 | Knight |
| 2004/0078075 A1 | 4/2004 | Koziol |
| 2004/0080239 A1 | 4/2004 | Gupta et al. |
| 2005/0027355 A1 | 2/2005 | Murakami |
| 2005/0031697 A1 | 2/2005 | Vehige et al. |
| 2005/0033420 A1 | 2/2005 | Christie et al. |
| 2005/0046794 A1 | 3/2005 | Silvestrini et al. |
| 2005/0049621 A1 | 3/2005 | Feingold et al. |
| 2005/0080485 A1 | 4/2005 | Nigam |
| 2005/0119738 A1 | 6/2005 | Nigam |
| 2005/0124983 A1 | 6/2005 | Frey et al. |
| 2005/0143812 A1 | 6/2005 | Paul et al. |
| 2005/0182488 A1 | 8/2005 | Peyman |
| 2005/0187621 A1 | 8/2005 | Brady |
| 2005/0228376 A1 | 10/2005 | Boomer et al. |
| 2006/0079959 A1 | 4/2006 | Christie et al. |
| 2006/0079960 A1 | 4/2006 | Christie et al. |
| 2006/0113054 A1 | 6/2006 | Silvestrini |
| 2006/0184243 A1 | 8/2006 | Yilmaz |
| 2006/0235514 A1 | 10/2006 | Silvestrini |
| 2006/0241751 A1 | 10/2006 | Marmo et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271027 A1 | 11/2006 | Silvestrini et al. |
| 2006/0271176 A1 | 11/2006 | Christie et al. |
| 2006/0271177 A1 | 11/2006 | Christie et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0016234 A1 | 1/2007 | Daxer |
| 2007/0219542 A1 | 9/2007 | Yahagi |
| 2007/0225691 A1 | 9/2007 | Silvestrini et al. |
| 2008/0151183 A1 | 6/2008 | Altmann |
| 2009/0059168 A1 | 3/2009 | Miller et al. |
| 2009/0069817 A1 | 3/2009 | Peyman |
| 2009/0222086 A1 | 9/2009 | Lui et al. |
| 2011/0040376 A1 | 2/2011 | Christie et al. |

FOREIGN PATENT DOCUMENTS

| | | |
|---|---|---|
| FR | 369 993 | 1/1907 |
| FR | 2599156 | 5/1986 |
| FR | 2649605 | 1/1991 |
| GB | 1 026 839 | 4/1966 |
| GB | 1276003 | 6/1972 |
| JP | 62167343 A | 7/1987 |
| JP | 03-001857 | 1/1991 |
| JP | 04-158859 | 6/1992 |
| JP | 07-178125 | 7/1995 |
| JP | 07-265340 | 10/1995 |
| RU | 2138837 C1 | 9/1999 |
| SU | 1380743 A1 | 3/1998 |
| WO | WO 94/05232 | 3/1994 |
| WO | WO 94/23327 | 10/1994 |
| WO | WO 95/02356 | 1/1995 |
| WO | WO 95/03747 | 2/1995 |
| WO | WO 95/08135 | 3/1995 |
| WO | WO 96/35397 | 11/1996 |
| WO | WO 97/48004 | 12/1997 |
| WO | WO 97/48005 | 12/1997 |
| WO | WO 99/07309 | 2/1999 |
| WO | WO 00/52516 A2 | 9/2000 |
| WO | WO 00/52516 A3 | 9/2000 |
| WO | WO 01/19364 | 3/2001 |
| WO | WO 02/27388 | 4/2002 |
| WO | WO 02/102241 A2 | 12/2002 |
| WO | WO 03/030763 A1 | 4/2003 |
| WO | WO 2004/050132 | 6/2004 |
| WO | WO 2004/105588 A2 | 12/2004 |
| WO | WO 2006/047698 | 5/2006 |
| WO | WO 2008/036671 | 3/2008 |

OTHER PUBLICATIONS

Accommodation Responses and Ageing. Heron et al. IOVS, Nov. 1999, vol. 40, No. 12, pp. 2872-2883.
Accommodative responses to anisoaccommodative targets. Koh et al. Ophthal. Physiol. Opt. vol. 18, No. 3, pp. 254-262, 1998.
Accommodation responses to flickering stimuli. Chauhan et al. Ophthal. Physiol. Opt. vol. 16. No. 5, pp. 391-408, 1996.
Accommodation to perceived depth in stereo tests. Koh et al. Ophthal. Physiol. Opt. vol. 18, No. 3, pp. 279-284, 1998.
Age Changes in the Interactions between the Accommodation and Vergence Systems. Heron et al. Optometry and Vision Science. vol. 78, No. 10, Oct. 2001.
Can Accommodation be Surgically Restored in Human Presbyopia? Glasser, Adrian. Optometry and Vision Science, vol. 76, No. 9, Sep. 1999.
Changes in the static accommodation response with age. Kalsi et al. Ophthal. Physiol. Opt. vol. 21, No. 1, pp. 77-84, 2001.
Choice of Spatial Frequency for Contrast Sensitivity Evaluation After Corneal Refractive Surgery. Montes-Mico et al. Journal of Refractive Surgery, vol. 17: Nov./Dec. 2001: pp. 646-651.
Choyce, P. "Implants with Coloured and Opaque Portions: Implants with Built-In Stenopeic Aperture," pp. 21-26 "Uniocular Aphakia Corrected by Anterior Chamber Implants with Built-In Stenipeic Aperture," pp. 132-136.
Clinical Characteristics of Lamellar Channel Deposits After Implementation of Intacs. Ruckhofer et al. J Cataract Refract Surg, vol. 26, Oct. 2000: pp. 1473-1479.
Contemporary Polymer Applications for Corneal Surgery. McCarey, Bernard E. pp. 504-505.
Dynamics of the accommodation response to abrupt changes in target vergence as a function of age. Heron et al. Vision Research 41 (2001) 507-519.
Eight Years Experience with Permalens Intracorneal Lenses in Non-human Primates. Werblin et al. Refractive & Corneal Surgery, vol. 8, Jan./Feb. 1992, pp. 12-21.
EP 00 913659.9 Examination Report, dated Jul. 20, 2006, 5 pp.
Errors in determining the direction of the visual axis in the presence of defocus. Atchison et al. Ophthal. Physiol. Opt., vol. 18, No. 5, pp. 463-467,1998.
Groppi, J. J. "New Aspects in the Fitting of the Multi-Range Bifocal Contact Lens" Contacto, vol. 15:22-29 1971.
Holes in Clear Lenses Demonstrate a Pinhole Effect. Zacharia et al. Arch Ophthalmol, vol. 106, Apr. 1988, pp. 511-513.
Human Visual System- Image Formation. Roorda, Austin. pp. 539-557.
Intra-Ocular Lenses and Implants. Choyce, Peter. Chpts.4 & 17, 1964.
Intrastromal Crystalline Deposits Following Hydrogel Keratophakia in Monkeys. Parks et al. Cornea 12(1): 29-34,1993.
Lipid Deposits Posterior to Impermeable Intracornel Lenses in Rhesus Monkeys: Clinical, Histochemical, and Ultrastructural Studies. Rodrigues et al. Refractive & Corneal Surgery, vol. 6, Jan./Feb. 1990: DO. 32-37.
Miller et al. "Quantification of the Pinhole effect" Perspectives in Refraction, vol. 21:347-350 1977.
Near vision, lags of accommodation and myopia. Charman, W. N. Ophthal. Physiol. Opt., vol. 19, No. 2, pp. 126-133, 1999.
On the linearity of accommodation dynamics. Charman, W. N. Vision Research 40 (2000) 2057-2066.
Optical Modeling of Contact Lens Performance Final Report Covering Period Jul. 15, 1994-Mar. 31, 1995. Grivenkamp et al. For Pilkington Barnes Hind, Issued Apr. 5, 1995.
Optometric Clinical Practice Guideline Care of the Patient With Presbyopia: Reference Guide for Clinicians. Mancil et al. Mar. 20, 1998.
PCT/US00/05136 International Preliminary Examination Report, dated Mar. 15, 2001, 5 pp.
PCT/US00/05136 International Search Report, dated Aug. 18, 2000, 9 pp.
PCT/US04/16914 International Search Report and Written Opinion, dated Apr. 13, 2005, 9 pp.
PCT/US04/16914 Preliminary Report on Patentability, dated Dec. 15, 2005, 6 pp.

PermaVision intracorneallens shows promise for hyperopia. Kronemyer, Bob. Ocular Surgery News: Jan. 1, 2003; p. 8.
Refractive keratoplasty with intrastromal hydrogel lenticular implants. McCarey et al. Invest. Ophthalmol. Vis. ScL, Jul. 1981, pp. 107-115.
Retinal Image Quality in the Human Eye as a Function of the Accommodation. Lopex-Gil et al. Vision Research, vol. 38, No. 19,Jul. 3, 1998, pp. 1-11.
Rosenbloom "The Controlled-Pupil Contact Lens in Low Vision Problems" Journal of the American Optometric Association, pp. 836, 838, 840 1969.
Subjective Depth-of-Focus of the Eye. Atchison et al. Optometry and Vision Science, vol. 74, No. 7, Jul. 1997, pp. 511-520.
Takahashi, E. "Use and Interpretation of the Pinhole Test" the Optometric Weekly, pp. 83-86 1965.
Wesley, N. K. "Research on the Multi-Range Lens," pp. 18, 20-24.
U.S co-pending U.S. Appl. No. 12/182,038, filed Jul. 29, 2008.
Accomodation and acuity under night-driving illumination levels. Arumi et al. Opthal. Physiol. Opt. vol. 17, No. 4, pp. 291-299,1997.
Accomodation dynamics as a function of age. Heron et al. Opthal. Physiol. Opt. 2002 22:389-396.
Corneal Topography: The State of the Art, "Alignment of Videokeratographs," Mandell et al. Chpt. 2, pp. 17-23, Jan. 1995.
Anterior Ciliary Sclerotomy for Treatment of Presbyopia: A Prospective Controlled Study. Hamilton et al. Ophthalmology, vol. 109, No. 11: Nov. 2002: pp. 1970-1977.
Dynamic retinoscopy and accomodation. Whitefoot et al. Ophthal. Physiol. Opt. vol. 12, Jan. 1992, pp. 8-17.
Eduard Jaeger's Test-Types (Schrift-Scalen) and Historical Development of Vision Tests. Runge, Paul E. Tr. Am. Ophth. Soc. vol. 98, 2000: 375.
EPO Supplementary Search Report for Application No. 04753697.4, dated Apr. 21, 2008 in 3 pages.
Evaluate surgical routine to determine DLK cause, surgeon advises. Piechocki, Michael. Ocular Surgery News: Refractive Surgery, Jan. 1, 2003: p. 14.
Explanation for the observation of isogyres in crystalline lenses viewed between crossed polarizers. Opthal. Physiol. Opt., vol. 13, Apr. 1993, pp. 209-211.
Flap Measurements With the Hansatome Microkeratome. Spadea et al. Journal of Refractive Surgery, vol. 18, Mar./Apr. 2002: pp. 149-154.
Focused and divided attention in stereoscopic deth. Wickens et al. SPIE, vol. 1256 Stereoscopic Displays and Applications (1990); pp. 28-34.
Hybrid diffractive-refractive achromatic spectacle lenses. Charman, W. N. Opthal. Physiol. Opt., vol. 14, Oct. 1994: pp. 389-392.
Imaging in the 21st century. Charman, W. N. Ophthal. Physiol. Opt., vol. 18, No. 2, pp. 210-223,1998.
International Search Report and Written Opinion in PCT Application No. PCT/US/2005/043108 dated Aug. 30, 2006 in 16 pages.
Intraocular pressure after excimer laser myopic refractive surgery. Montes-Mico et al. Ophthal. Physiol. Opt., vol. 21, No. 3, pp. 228-235, 2001.
Mastel Precision: Fiber Optic Ring Illuminator (Product Nos. 3776 & 4050) US Patent No. 5312393 User Manual. Rev: A02: Jan. 11, 1995, pp. 1-25.
Mastel Precision: The Ring Light. http://www.mastel.com/ring_light.html. Jul. 28, 2003.
Measurement of the wave-front aberration of the eye by a fast psychophysical procedure. He et al. J. Opt. Soc. Am. A, vol. 15, No. 9: Sep. 1998, pp. 2449-2455.
Microstructural Changes in Polyester Biotextiles During Implantation in Humans. King et al. NC State University: JTATM, vol. 1, Issue 3, Spring 2001, pp. 1-8.
New Visual Acuity Charts for Clinical Research. Ferris et al. American Journal of Ophthalmology, 94: 91-96, 1982.
Night myopia and driving. Charman, W. N. Ophthal. Physiol. Opt., vol. 16, No. 6, p. 474-485, 1996.
Notch in contrast sensitivity function of optical origin: diffraction effects of acrylic filters. Irving et al. Ophthal. Physiol. Opt., vol. 13, Apr. 1993: pp. 179-182.

On modeling the causes of presbyopia. Glasser, A. Vision Research 41(2001) 3083-3087.

Optical Aspects of Tolerances to Uncorrected Ocular Astigmatism. Charman et al. Optometry and Vision Science, vol. 70, No. 2: pp. 111-117, 1993.

PCT/US00/05136 Invitation to Pay Additional Fees, dated Jun. 16, 2000, 5 pp.

Perspectives in Refraction: Quantification of the Pinhole Effect. Miller et al. Survey of Ophthalmology, vol. 21, No. 4, Jan./Feb. 1977, pp. 347-350.

Poly(methyl methacrylate) model study of optical surface quality after excimer laser photo refractive keratectomy. Hauge et al. J Cataract Refract Surg., vol. 27, Dec. 2001, pp. 2026-2035.

Procyon: Marketing Information for Distributors: Pupil Measurement and Refractive Sugery (Samples from Academic Papers). pp. 1-17, 1994.

Simple parametric model of the human ocular modulation transfer function, A. Deeley et al. Ophthal. Physiol. Opt., vol. 11, Jan. 1991, pp. 91-93.

Surface Modification Properties of Parylene for Medical Applications, The. Wolgemuth, Lonny.Business Briefing: Medical Device Manfacturing & Technology 2002, pp. 1-4.

Surface tension control of collagen biomaterials by the selective hydrolysis of internal carboxyamides of the protein matrix. Revista Brasileira de Engenharia Biomedica, v. 15, n. 1-2, p. 55-61, Jan. 1999.

Surgeon: Severe corneal lesions after LASIK are not stage 4 DLK. Piechocki, Michael. Ocular SurgeryNews; Jan. 1, 2003, pp. 16-17.

Theoretical and practical performance of a concentric bifocal intraocular implant lens. Charman, W.N. Vision Research 38 (1998) 2841-2853.

Use of a digital infrared pupillometer to assess patient suitability for refractive surgery. Rosen et al. J Cataract Refract Surg., vol. 28: Aug. 2002. pp. 1433-1438.

Vision and driving—a literature review and commentary. Charman, W.N. Ophthal. Physiol. Opt., vol. 17, No. 5, pp. 371-391, 1997.

Binder et al., "Hydrogel keratophakia in non-human primates", Current Eye Research, vol. 1, No. 9, 1981/1982, pp. 535-542.

Cao et al., "Comparative study of the use of poly(glycolic acid), calcium alginate and pluronics in the engineering of autologous porcine cartilage", Polymers for Tissue Engineering, pp. 315-327, VSP 1998.

"Corneal Surgery" by L. Girard, The C.V. Mosby Publishing Company, London 1981 pp. 107-141.

"Epikeratophakia: Techniques, Compositions, and Clinical Results" by Werblin, Opthalmology, 1983, pp. 45-58.

Extended European Search Report in European Patent Application No. 10180819.4 dated Feb. 23, 2011 in 7 pages.

Griffith et al.; "Functional Human Corneal Equivalents Constructed from Cell Lines", Science, vol. 286, Dec. 10, 1999 pp. 2169-2172.

Iijima et al. "Formation of a spherical multicellular aggregate (spheroid) of animal cells in the pores of polyurethane foam as a cell culture substratum and its application to a hybrid artificial liver", Polymers for Tissue Engineering , pp. 273-286, VSP 1998.

"Keratomileusis and Keratophakia in the Surgical Correction of Aphakia" by Barraquer, Cataract Surgery and Special Techniques, prior to 1996 pp. 270-289.

"Lamellar Corneal Stromectomy for the Operative Treatment of Myopia" by Tadeusz Krwawicz, Notes, Cases, Instruments—1964, pp. 828-833.

Sally Pobojewski, "New U-developed laser performs high-precision corneal surgery", News and Information Services, The University Record, Jul. 16, 1997.

"Refractive Keratoplasty: Acute Morphologic Features," by Baumgarter et al, The CLAO Journal—Apr. 1985, vol. II, No. 2, pp. 163-169.

Karin R. Slettin, MD et al., "An in Vivo Model of Femtosecond Laser Intrastromal Refractive Surgery", Experimental Science, Opthalmic Surgery and Lasers, Nov./Dec. 1999, vol. 30, No. 9, pp. 742-749.

Subjective Sensitivity to Small Changes in the Contrast of a Suprathreshold Grating, The. Walsh et al. Vision Res., vol. 30, No. 1, pp. 163-193, 1990.

Swinger et al., "Keratophakia and Keratomileusis-Clinical Results", American Academy of Opthalmology, Aug. 1981, vol. 88, No. 8, pp. 709-715.

Yamauchi et al., "Cultivation of fibroblast cells on keratin coated substrata", Polymers for Tissue Engineering, pp. 329-340, VS 1998.

* cited by examiner

SYSTEM AND METHOD FOR INCREASING THE DEPTH OF FOCUS OF THE HUMAN EYE

RELATED APPLICATIONS

This application is a divisional application of U.S. patent application Ser. No. 11/284,791, filed Nov. 22, 2005, now U.S. Pat. No. 7,404,638, which is a divisional application of U.S. patent application Ser. No. 10/729,200, filed Dec. 5, 2003, now U.S. Pat. No. 6,966,648, which is a divisional of U.S. patent application Ser. No. 10/384,957, filed Mar. 10, 2003, now U.S. Pat. No. 6,874,886, which is a divisional of U.S. patent application Ser. No. 09/516,258, filed Feb. 29, 2000, now U.S. Pat. No. 6,554,424, which claimed priority from provisional U.S. Patent Application Ser. No. 60/122,001, filed Mar. 1, 1999, entitled "SCREENING TECHNIQUES AND DEVICES USED PRIOR TO THE INSERTION OF A CORNEAL ANNULUS INLAY;" provisional U.S. Patent Application Ser. No. 60/124,345, filed Mar. 15, 1999, entitled "NEW METHOD OF INCREASING THE DEPTH OF FOCUS OF THE HUMAN EYE;" and provisional U.S. Patent Application Ser. No. 60/138,110, filed Jun. 7, 1999, entitled "WOVEN ANNULAR MASK CORNEAL INLAY." This application is also a divisional application of U.S. patent application Ser. No. 09/516,258, filed Feb. 29, 2000, now U.S. Pat. No. 6,554,424. The disclosures of all these applications are incorporated herein, in their entirety, by reference.

BACKGROUND OF THE INVENTION

1. Field of the Invention

The invention generally relates to ophthalmic lenses and, more particularly, the invention relates to ophthalmic lenses for increasing the depth of focus of the human eye.

2. Description of the Related Art

It is well-known that the depth of focus of the human eye can be increased with the use of ophthalmic lenses with pinhole-like apertures substantially near the optical center of the lens. For example, U.S. Pat. No. 4,976,732 ("the '732 patent") discloses an ophthalmic lens with a pinhole-like aperture. In the '732 patent, a mask forms the pinhole-like aperture. In one embodiment, the mask is circular in shape. When the pupil is constricted, light enters the retina through the pinhole-like aperture. When the pupil is dilated, light enters the retina through the pinhole-like aperture and the outer edges of the mask.

In addition, U.S. Pat. No. 3,794,414 ("the '414 patent") discloses a contact lens with a pinhole-like aperture. In the '414 patent, the mask forming the pinhole-like aperture has radial slits and/or scalloped edges. In addition, the mask forming the pinhole-like aperture is two spaced-apart concentric circles. However, the radial slits, scalloped edges and two spaced-apart concentric circles promote light diffraction, which in turn reduces the contrast of the image.

In U.S. Pat. Nos. 4,955,904, 5,245,367, 5,757,458 and 5,786,883, various modifications to an ophthalmic lens with a pinhole-like aperture are disclosed. For example, the patents disclose use of an optical power for vision correction in the pinhole-like aperture, or use of an optical power for vision correction in the area outside the mask. In contrast, in U.S. Pat. No. 5,980,040, the mask is powered. In particular, the mask is powered to bend the light passing through the mask to impinge on the retina at a radial distance outside of the fovea. In other words, the mask is powered to "defocus" the light.

In each of these patents, the mask forming the pinhole-like aperture is made, in whole or in part, of a light absorptive material. A light-absorptive material is a material in which light is lost as it passes through the material, generally due to conversion of the light into another form of energy, e.g., heat.

SUMMARY OF THE INVENTION

In accordance with an embodiment of the invention, an ophthalmic lens comprises a lens body, an optic located in the lens body, the optic configured to produce light interference, and a pinhole-like optical aperture substantially in the center of the optic. In a further embodiment of the invention, the optic is configured to positively interfere with parallel light reaching the optic and negatively interfere with diverging light reaching the optic. In addition, some diverging light may pass through the optic. In this alternate embodiment of the invention, the optic is configured to spread out the diverging light passing through the optic.

In an alternate embodiment of the invention, an ophthalmic lens comprises a lens body, an optic located in the lens body, the optic configured to produce light scattering, and a pinhole-like optical aperture substantially in the center of the optic. In a further embodiment of the invention, the optic is configured to forward scatter parallel light reaching the optic and back scatter diverging light reaching the optic.

In another alternative embodiment of the invention, an ophthalmic lens comprises a lens body, an optic located in the lens body, the optic configured to produce light reflection, and a pinhole-like optical aperture substantially in the center of the optic. In an alternate embodiment of the invention, the optic is composed, in whole or in part, of a light reflective material.

In further embodiments of the inventions, the optic may be configured as a series of concentric circles, a weave, a pattern of particles, or a pattern of curvatures. In addition, the pinhole-like aperture includes an optical power for vision correction, and may have a diameter in the range of substantially 0.05 mm to substantially 5.0 mm. Further, the optic may have an outer diameter in the range of substantially 1.0 mm to substantially 8.0 mm. The optic may also be composed of a material having varying degrees of opacity, and the ophthalmic lens and the optic may be composed of a bio-compatible, non-dissolving material, such as polymethyl methacrylate or a medical polymer.

In accordance with another embodiment of the invention, a method for screening a patient for an ophthalmic lens, the ophthalmic lens having a pinhole-like optical aperture, comprises fitting each of the patient's eyes with a first contact lens, placing a mask on each of the first contact lens, the mask configured to produce a pinhole-like aperture in each of the first contact lens, fitting each of the patient's eyes with a second contact lens, the second contact lens being placed over the mask to hold the mask in a substantially constant position, and testing the patient's vision.

In further embodiments of the invention, the mask may be a light interference mask, a light scattering mask, or a light reflective mask. The first contact lens may include an optical power for vision correction. In addition, each of the first and second contact lenses may be soft contact lenses. Further, the mask for each of the patient's eyes may have a light absorption of substantially 100%. In the alternative, the mask for each of the patient's eyes may be composed of a polarized material.

In still further embodiments of the invention, the process of testing comprises testing the patient's acuity for distance vision under bright and dim lighting conditions, testing the patient's acuity for near vision under bright and dim lighting conditions, and testing the patient's contrast sensitivity under bright and dim lighting conditions. The process of testing may further comprise testing a patient's visual acuity using a night driving simulation. The night driving simulation may include a series of objects and road signs under bright and dim lighting conditions, as well as having the patient face a simulated oncoming automobile headlight.

In an alternate embodiment of the invention, the process of testing comprises replacing the mask in one of the patient's eyes with a mask having a light L absorption of substantially 85% or less, then, if needed, replacing the mask in the patient's other eye with a mask having a light absorption of substantially 85% or less. Further, the process of testing comprises, if needed, removing the mask from one of the patient's eyes.

In another alternate embodiment of the invention, the process of testing comprises placing an analyzer in the spectacle plane of one of the patient's eyes, the analyzer including a polarizing element, rotating the polarizing element to achieve an optimal balance of contrast and brightness, and determining the resultant light absorption of the mask. In addition, the process of testing may include evaluating the cosmetic appearance of the mask.

In accordance with a still another embodiment of the invention, a method for implanting a mask in a cornea, the mask configured to increase the depth of focus of the human eye, comprises removing the epithelial sheet, creating a depression in the Bowman's membrane, the depression being of sufficient depth and width to expose the top layer of the stroma and accommodate the mask, placing the mask in the depression, and placing the removed epithelial sheet over the mask. In a further embodiment of the invention, the depression may extend into the top layer of the stroma.

In an alternate embodiment of the invention, a method for implanting a mask in a cornea, the mask configured to increase the depth of focus of the human eye, comprises hinging open a portion of the Bowman's membrane, creating a depression in the top layer of the stroma, the depression being of sufficient depth and width to accommodate the mask, placing the mask in the depression, and placing the hinged Bowman's membrane over the mask.

In another alternate embodiment of the invention, a method for implanting a mask in a cornea, the mask configured to increase the depth of focus of the human eye, comprises creating a channel in the top layer of the stroma, the channel being in a plane parallel to the cornea's surface, and placing the mask in the channel. In this embodiment, the mask may be threaded into the channel, or the mask may be injected into the channel.

In still another alternate embodiment of the invention, a method for implanting a mask in a cornea, the mask configured to increase the depth of focus of the human eye, comprises penetrating the top layer of the stroma with an injecting device, and injecting the mask into the top layer of the stroma with the injecting device. In this embodiment, the injecting device may be a ring of needles. In addition, the mask may be a pigment, or the mask may be composed of pieces of pigmented material suspended in a bio-compatible medium. The pigmented material may be made of a medical polymer, e.g., suture material.

In one other alternate embodiment of the invention, a method for implanting a mask in a cornea, the mask configured to increase the depth of focus of the human eye, comprises hinging open a corneal flap, the corneal flap comprising substantially the outermost 20% of the cornea, placing the mask on the cornea, and placing the hinged corneal flap over the mask.

In still one other alternate embodiment of the invention, a method for implanting a mask in a cornea, the mask configured to increase the depth of focus of the human eye, comprises creating a pocket in the stroma, the pocket being of sufficient size to accommodate the mask, and placing the mask in the created pocket.

In further embodiments of the inventions, the mask may be a light interference optic, a light scattering optic, or a light reflective optic. In addition, the mask may block visual aberrations. In addition, after surgery, a contact lens may be placed over at least the affected portion of the cornea.

BRIEF DESCRIPTION OF THE DRAWINGS

The foregoing and other objects and advantages of the invention will be appreciated more fully from the following further description thereof with reference to the accompanying drawings wherein.

DETAILED DESCRIPTION OF THE PREFERRED EMBODIMENT

In accordance with an embodiment of the invention, an ophthalmic lens (e.g., a contact lens, an intra ocular lens, a corneal inlay lens, etc.) increases the depth of focus of the human eye through the use of an optic. The optic surrounds a pinhole-like optical aperture near the optical center of the lens. The pinhole-like aperture in conjunction with the optic increases the depth of focus of the human eye. In particular, the optic increases the depth of focus of the human eye using light interference, light scattering, light reflection, light absorption and/or a combination of one or more of these properties. An optic configured in accordance with the various embodiments of the invention is referred to as a Paraxial Adaptive Optic™.

Figure 1A:
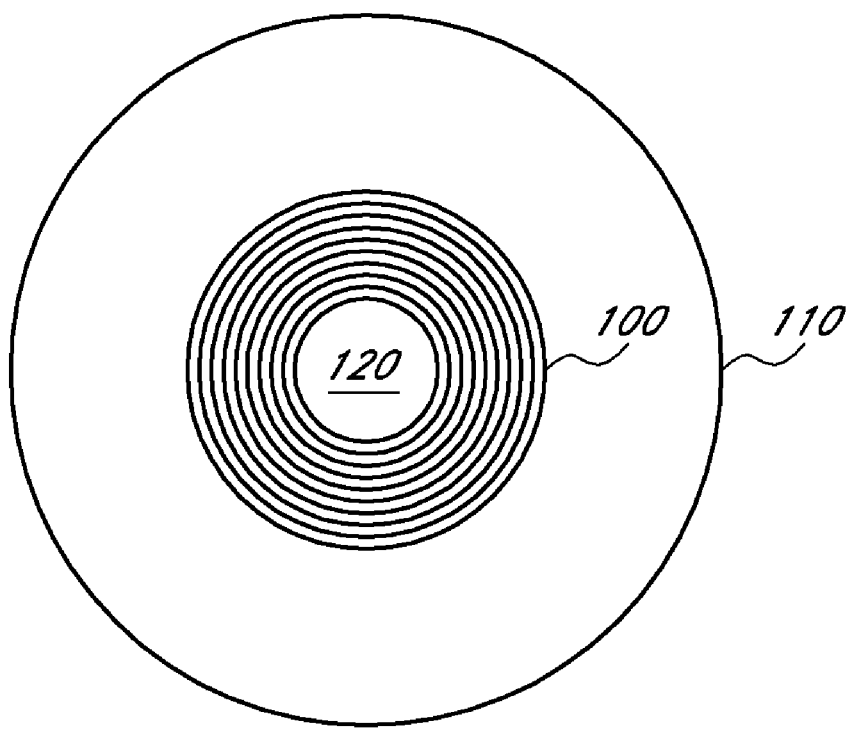
FIGS. 1a and 1b show an exemplary ophthalmic lens with an exemplary optic configured to produce light interference.
Figure 1B:
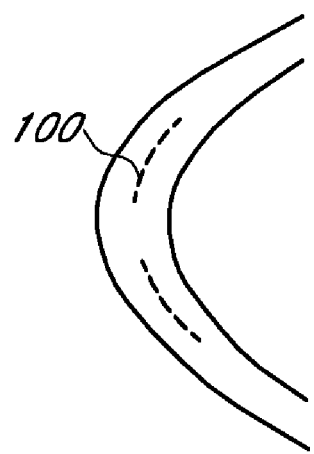

FIGS. 1a and 1b show an exemplary ophthalmic lens with an exemplary optic configured to produce light interference. FIG. 1a shows a front view of the exemplary ophthalmic lens. FIG. 1b shows a side view of the exemplary optic implanted in the cornea of a human eye.

Light interference is the additive process in which the amplitude of two or more overlapping light waves is either attenuated or reinforced. For example, when two overlapping light waves are in-phase (the crest and trough of one wave coincides with the crest and trough of the other wave), then the amplitude of the resultant light wave is reinforced. This type of interference is referred to as positive interference. In contrast, when two overlapping light waves are out-of-phase (the crest of one wave coincides with the trough of the other wave), then the amplitude of the resultant light wave is attenuated. This type of interference is referred to as negative interference. Of course, light interference also occurs between the two extremes of in-phase and out-of-phase.

As shown in FIGS. 1a and 1b, optic 100 is located substantially in the center of lens body 110. Optic 100 surrounds optical aperture 120 located near the optical center of lens body 110. The specific location of optical aperture 120 in lens body 110 varies in accordance with the patient's eye. Specifically, optical aperture 120 is positioned in lens body 10 to be concentric with the patient's pupil.

In operation, optical aperture 120 increases the depth of focus of the human eye via a "pinhole effect." In particular, optical aperture 120 increases depth of focus by limiting the light reaching the retina to plane wavefront light. In photonics, a wavefront is a surface connecting all points equidistant from a source. Plane wavefront light is relatively parallel light, e.g., light from a distant source. It is "relatively" parallel light because, in reality, even light from a distant star is diverging light. In contrast, convex wavefront light is relatively diverging light, e.g., light from a near source. It is easier for the human eye to focus plane wavefront light because the crystalline lens of the human eye can focus parallel light on the retina with little or no accommodation. In accommodation, the crystalline lens, through the action of the ciliary muscles, thickens and, thereby, changes its degree of curvature.

In order to achieve a useful "pinhole effect," optical aperture 120 should have a diameter in the range of substantially 0.05 millimeters ("mm") to substantially 5.0 mm. In addition, in order to aid examination of the retina and increase brightness when the pupil is dilated, the outer diameter of optic 100 should be in the range of substantially 1.0 mm to substantially 8.0 mm. Moreover, to further improve vision, optical aperture 120 may include an optical power for vision correction, e.g., correction for near vision, correction for distance vision, correction for intermediate vision, etc. Also, the area outside optic 100 may include an optical power for vision correction.

In operation, optic 100 increases the depth of focus of the human eye via its configuration. In particular, optic 100 is configured to produce light interference via a series of concentric circles. Specifically, optic 100 is configured to reinforce relatively parallel light and attenuate relatively diverging light. When optic 100 attenuates less than all of the relatively diverging light, then optic 100 is further configured to spread out the diverging light that passes through optic 100, i.e., weakening the diverging light passing through optic 100. Thus, because diverging light is attenuated and/or weakened, the "pinhole effect" of optical aperture 120 is increased for relatively near objects, producing a higher contrast depth of focus image of relatively near objects. Moreover, because parallel light is reinforced, the "pinhole effect" of optical aperture 120 is reduced, producing a brighter image of relatively distant objects.

Optic 100 is also configured to effect the chromatic aberration of the human eye. The human eye's chromatic aberration, in which the size of an image appears to change when the color of the image is changed, results from the normal increase in refractive index toward the blue end of the color spectrum. In optic 100, the increase in refractive index is toward the red end of the color spectrum. Thus, optic 100 may reduce or cancel the chromatic aberration of the human eye.

Further, optic 100 is configured to meet the specific needs of the patient. For example, a person of skill in the art understands that, among other things, the addition of concentric circles, the removal of concentric circles, the change in spacing between concentric circles, the varying of spacing between concentric circles, and the shape of the concentric circles (e.g., oval, round, elliptical, etc.) would influence the light interference properties of optic 100.

Figure 2A:
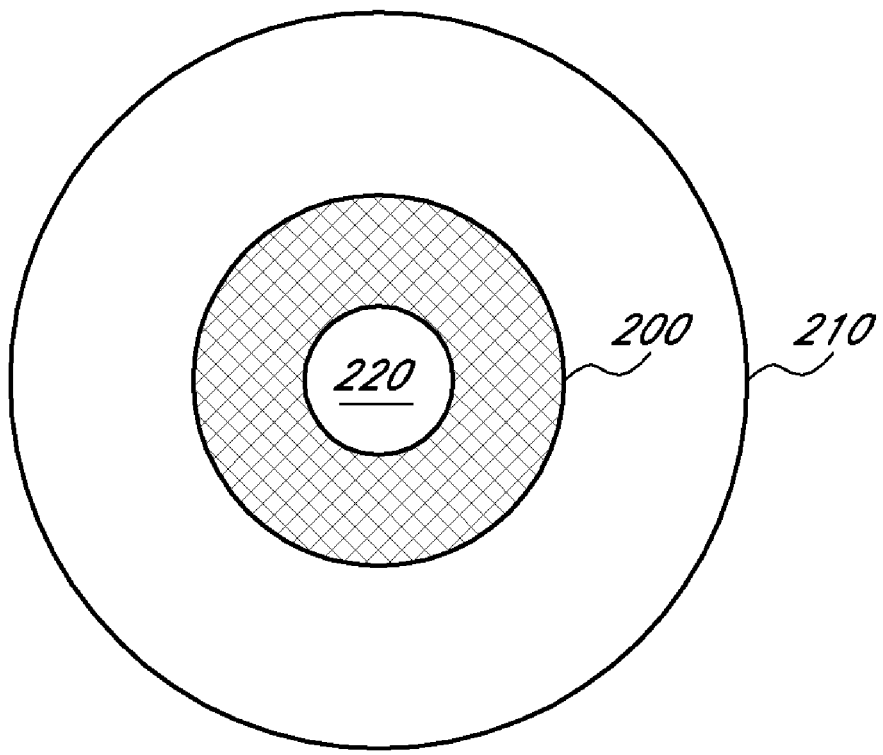
FIGS. 2a and 2b show another exemplary ophthalmic lens with another exemplary optic configured to produce light interference.
Figure 2B:
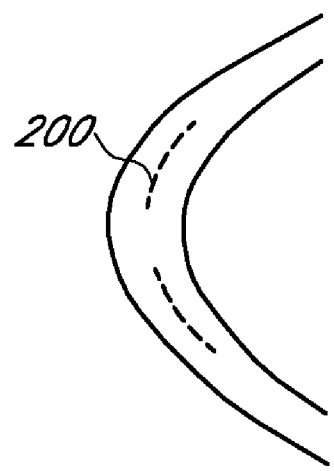

FIGS. 2a and 2b show another exemplary ophthalmic lens with another exemplary optic configured to produce light interference. In this exemplary embodiment, optic 200 is configured to produce light interference via a weave. As discussed in regard to optic 100, the weave reinforces relatively parallel light and attenuates relatively diverging light. Depending on the weave's material, the weave may also absorb light coming into contact with the weave's material. FIG. 2a shows a front view of the exemplary ophthalmic lens. FIG. 2b shows a side view of the exemplary optic implanted in the cornea of a human eye.

As discussed in regard to optic 100, optic 200 is configured to meet the specific needs of the patient. For example, a person of skill in the art understands that, among other things, the density of the weave would influence the light interference properties of optic 200.

Figure 3A:
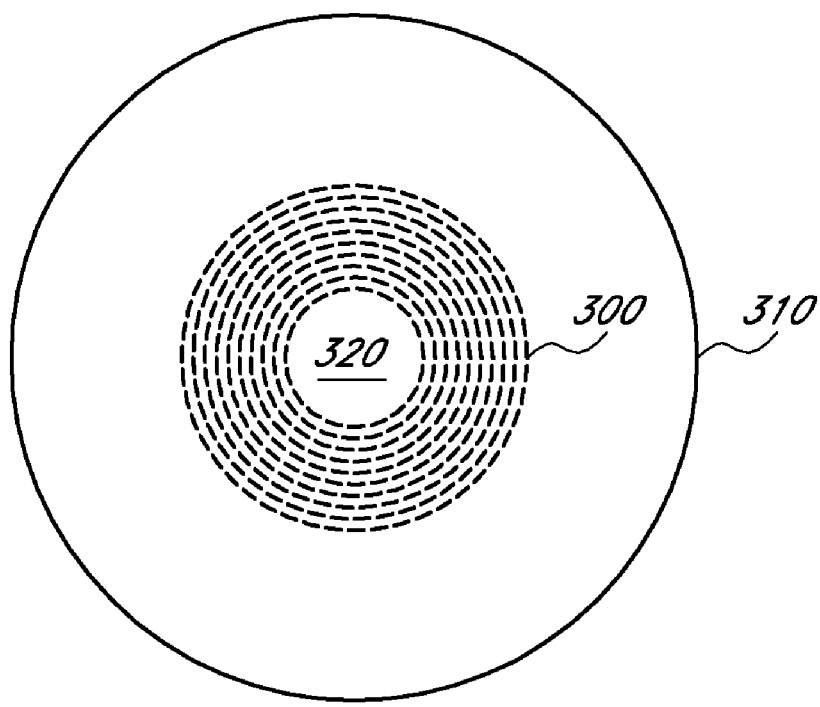
FIGS. 3a and 3b show an exemplary ophthalmic lens with an exemplary optic configured to produce light scattering.
Figure 3B:
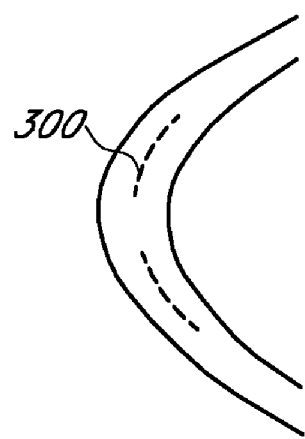

FIGS. 3a and 3b show an exemplary ophthalmic lens with an exemplary optic configured to produce light scattering. FIG. 3a shows a front view of the exemplary ophthalmic lens. FIG. 3b shows a side view of the exemplary optic implanted in the cornea of a human eye.

In general, light scattering is the deflection of light upon interaction with a medium. Light is forward scattered when, upon interaction with a medium, it is deflected through angles of 90°. or less with respect to the original direction of motion. Light is back scattered when, upon interaction with a medium, it is deflected through angles in excess of 90°. with respect to the original direction of motion.

As shown in FIGS. 3a and 3b, optic 300 is located substantially in the center of lens body 310. Optic 300 surrounds optical aperture 320 located near the optical center of lens body 310. The specific location of optical aperture 320 in lens body 310 varies in accordance with the patient's eye. Specifically, optical aperture 320 is positioned in lens body 310 to be concentric with the patient's pupil.

As discussed in regard to optical apertures 120 and 220, optical aperture 320 increases the depth of focus of the human eye via a "pinhole effect." Similarly, as discussed in regard to optics 100 and 200, optic 300 increases the depth of focus of the human eye via its configuration. In particular, optic 300 is configured to produce light scattering via a pattern of particles. Specifically, optic 300 is configured to forward scatter relatively parallel light and back scatter relatively diverging light. Thus, because diverging light is back scattered, the "pinhole effect" of optical aperture 320 is increased for relatively near objects, producing a higher contrast depth of focus image of relatively near objects. Moreover, because parallel light is forward scattered, the "pinhole effect" of optical aperture 320 is reduced, producing a brighter image of relatively distant objects.

Further, optic 300 is configured to meet the specific needs of the patient. For example, a person of skill in the art understands that, among other things, the light absorption of the particles, the index of refraction of the particles, the index of refraction of the media surrounding the particles, the size of the particles, and the space between the particles would influence the light scattering properties of optic 300. In addition, optic 300 may be configured to produce light interference, as discussed in regard to optics 100 and 200.

Figure 4A:
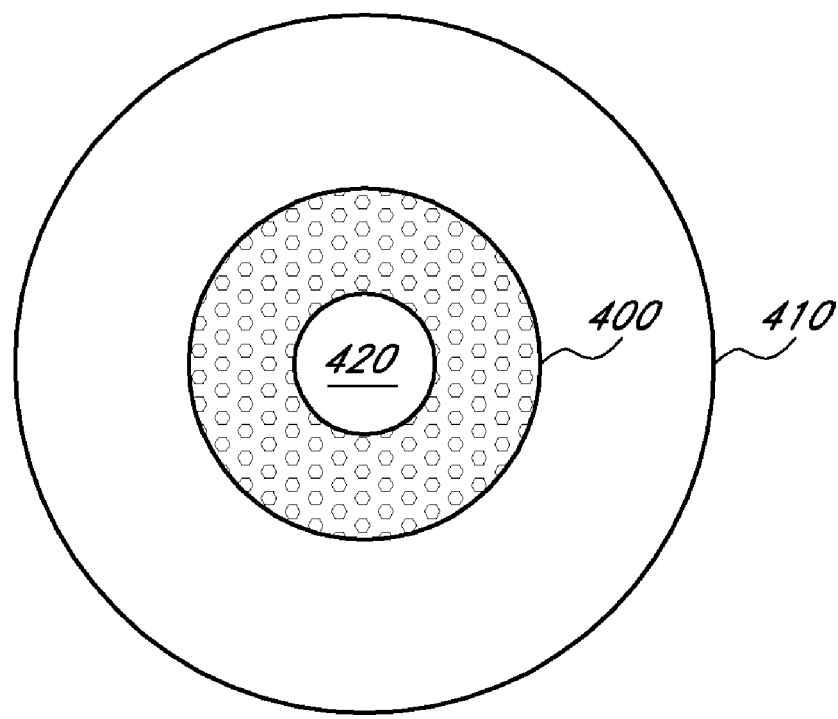
FIGS. 4a and 4b show an exemplary ophthalmic lens with an exemplary optic configured to produce light reflection.
Figure 4B:
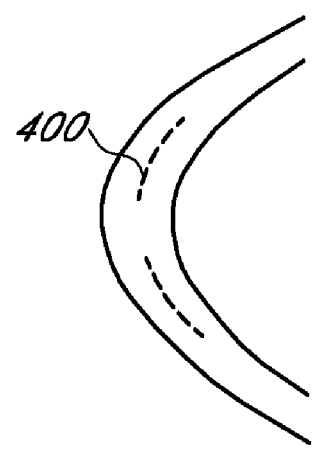

FIGS. 4a and 4b show an exemplary ophthalmic lens with an exemplary optic configured to produce light reflection.

FIG. 4a shows a front view of the exemplary ophthalmic lens. FIG. 4b shows a side view of the exemplary optic implanted in the cornea of a human eye.

Optic 400 is located substantially in the center of lens body 410. Optic 400 surrounds optical aperture 420 located near the optical center of lens body 410. The specific location of optical aperture 420 in lens body 410 varies in accordance with the patient's eye. Specifically, optical aperture 420 is positioned in lens body 410 to be concentric with the patient's pupil.

As discussed in regard to optical apertures 120, 220 and 320, optical aperture 420 increases the depth of focus of the human eye via a "pinhole effect." Similarly, as discussed in regard to optics 100, 200 and 300, optic 400 increases the depth of focus of the human eye via its configuration. In particular, optic 400 is configured to reflect light, in whole or in part, via a pattern of curvatures. Specifically, optic 400 is configured to favor transmission of the light to which the retinal rods are more sensitive, i.e., dim light and/or blue light, and to block the light to which retinal cones are more sensitive, i.e., bright light. Thus, because bright light is blocked, the "pinhole effect" of optical aperture 420 is increased for relatively near objects, producing a higher contrast depth of focus image of relatively near objects. Moreover, because dim light and/or blue light is transmitted, the "pinhole effect" of optical aperture 420 is reduced, producing a brighter image of relatively distant objects.

In an alternate embodiment, optic 400 may be composed, in whole or in part, of a light reflective material. A light reflective material is a material that, in whole or in part, reflects back light coming into contact with the material.

Further, optic 400 may be configured to meet the specific needs of the patient. For example, a person of skill in the art understands that, among other things, the type of material, the thickness of material, and the curvature of material would influence the light reflective properties of optic 400. In addition, optic 400 may be configured to produce light interference and/or light scattering, as discussed in regard to optics 100, 200 and 300, respectively.

In a particular embodiment of the ophthalmic lens described in FIG. 4, optic 400 is composed of a light reflective material with a peak transmission of substantially 550 nanometers ("nm"). A light-adapted retina has a peak transmission at 550 nm. In contrast, a dark-adapted retina has a peak transmission at 500 nm. Thus, an optic with a peak transmission of substantially 550 nm filters out more light with a peak transmission of 500 nm, i.e., bright light, than light with a peak transmission of 550 nm, i.e., dim light. Thus, as discussed above, because bright light is blocked, the "pinhole effect" of optical aperture 420 is increased for relatively near objects, producing a higher contrast depth of focus image of relatively near objects. Moreover, because dim light is transmitted, the "pinhole effect" of optical aperture 420 is reduced, producing a brighter image of relatively distant objects.

Further, this particular embodiment of optic 400 may be configured to meet the specific needs of the patient. For example, a person of skill in the art understands that, among other things, the peak transmission of the mask may be changed, e.g., to a peak transmission of 500 nm. In addition, the mask may be composed of material, other than light reflective material, which also allows the desired peak transmissions.

In alternate embodiments, the optic is composed of biocompatible, non-dissolving material, e.g., polymethyl methacrylate or medical polymers. In addition, the optic may be composed, in whole or in part, of a light reflective material or, in whole or in part, of a light absorptive material. Further, the optic may be composed, in whole or in part, of a material having varying degrees of opacity. The optic may also be configured to produce light interference, light-scattering and light reflection, or some combination of one or more of these properties. Moreover, the optic may be colored to match the color of a patient's iris.

In accordance with a further embodiment of the invention, a patient interested in an ophthalmic lens with a pinhole-like aperture is screened using soft contact lenses and a mask, referred to as a pinhole screening device. The mask may be an optic as described in the prior art, an optic as described herein, or an optic combining one or more of these properties. After insertion of the pinhole screening device, the patient's vision is tested.

Figure 5:
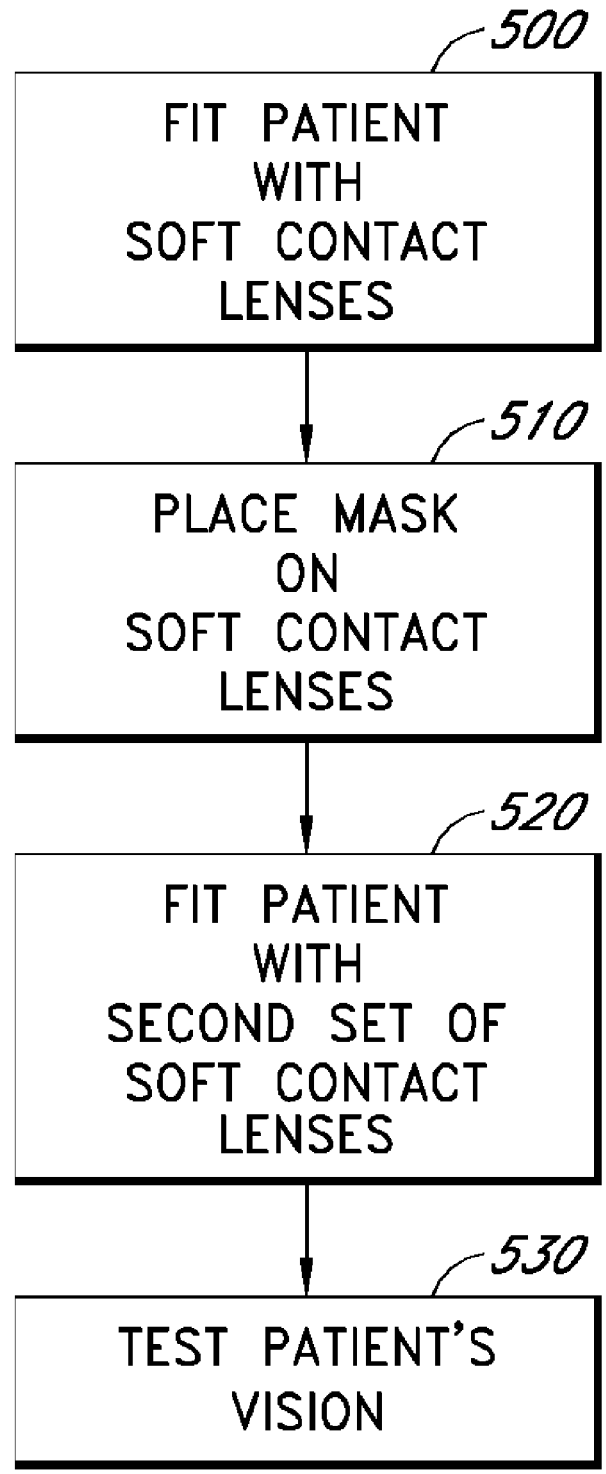
FIG. 5 shows an exemplary process for screening a patient interested in an ophthalmic lens with a pinhole-like aperture using an exemplary pinhole screening device.

FIG. 5 shows an exemplary process for screening a patient interested in an ophthalmic lens with a pinhole-like aperture using an exemplary pinhole screening device. The process begins at step 500, in which the patient is fitted with soft contact lenses, i.e., a soft contact lens in placed in each of the patient's eyes. If needed, the soft contact lenses may include vision correction. Next, at step 510, a mask is placed on the soft contact lenses. The mask should be placed concentric with the patient's pupil. In addition, the curvature of the mask should parallel the curvature of the patient's cornea. The process continues at step 520, in which the patient is fitted with a second set of soft contact lenses, i.e., a second soft contact lens is placed over the mask in each of the patient's eyes. The second contact lens holds the mask in a substantially constant position. Last, at step 530, the patient's vision is tested. During testing, it is advisable to check the positioning of the mask to ensure it remains concentric with the patient's pupil.

A test of the patient's vision may include testing the patient's acuity for distance vision under bright and dim lighting conditions, testing the patient's acuity for near vision under bright and dim lighting conditions, and testing the patient's contrast sensitivity under bright and dim lighting conditions. In addition, the test may include testing the patient's visual acuity using a night driving simulation. A night driving simulation may include a series of objects and road signs under bright and dim lighting conditions, as well as a simulated oncoming automobile headlight.

The test of the patient's vision may further include changing the mask. For example, the test might first be conducted using, in each of the patient's eyes, a mask having a light absorption of substantially 100%. If, for example, the patient experiences a sense of dimness, the mask in one of the patient's eyes may be replaced with a mask having a light absorption of substantially 85%. If, for example, the sense of dimness continues, the mask in the patient's other eye may be replaced with a mask having a light absorption of substantially 85%. Then, for example, if the sense of dimness continues, the mask may be removed from one of the patient's eyes.

In the alternate, the mask in one of the patient's eyes may be replaced with a mask having a light absorption less than substantially 85%. If, for example, the patient experiences a sense of dimness with a mask having a light absorption of substantially 100%, then the mask in one of the patient's eyes may be replaced with a mask having a light absorption of substantially 75%. If, for example, the sense of dimness continues, the mask in the patient's other eye may be replaced with a mask having a light absorption of substantially 75%. Then, for example, if the sense of dimness continues, the 75% mask may be replaced with a mask having a light absorption of substantially 50%.

As can be seen, there are numerous permutations for thoroughly screening the patient to find the optimal balance of contrast and brightness. In effect, the, mask in each of the patient's eyes is replaced, every other time, with a mask having a different light absorption than the replaced mask. This process continues until the optimal balance of contrast and brightness is found.

The process for changing the mask while testing the patient's vision also includes changing from an optic as described in the prior art to an optic as described herein. In addition, various mask configurations may be used. For example, an optic having both light interference and light scattering may be used, or an optic having both light reflective and light absorptive properties may be used. Once again, the numerous permutations allow for thoroughly screening the patient to find the optimal balance of contrast and brightness prior to, for example, the doctor placing a customized order or the patient undergoing invasive surgery.

The test of the patient's vision may also include evaluating the cosmetic appearance of the mask. For example, if the patient is dissatisfied with the appearance of the mask, the mask can be replaced with a mask of appropriate configuration colored to match the patient's iris.

In an alternate testing process, the mask placed on the soft contact lens in each of the patient's eyes is composed of a polarized material. A polarized material has a light absorption of substantially 50%. Then, an analyzer, which contains a polarized element, is used to help calculate the patient's optimal light absorption properties for the mask. In the process, the analyzer is placed in the spectacle plane of one of the patient's eyes and the polarized element in the analyzer is rotated until the patient experiences an optimal balance of contrast and brightness. The process may be repeated for the patient's other eye.

Using the analyzer, the doctor may now calculate the resultant light absorption of the mask. If desired, a mask of similar light absorption, whether it be an optic as described in the prior art, an optic as described herein, or an optic combining one or more of these properties, can now be placed between the contact lenses in each of the patient's eyes and the patient's vision tested, as described above.

In accordance with a still further embodiment of the invention, a mask is surgically implanted into the eye of a patient interested in increasing his or her depth of focus. For example, the patient may suffer from presbyopia, a condition in which the crystalline lens can no longer accommodate near vision because of a loss of elasticity in the lens or a weakness in the ciliary muscle. The mask may be an optic as described in the prior art, an optic as described herein, or an optic combining one or more of these properties. Further, the mask may be configured to correct visual aberrations. To aid the surgeon surgically implanting a mask into a patient's eye, the mask may be pre-rolled or folded for ease of implantation.

The mask may be implanted in several locations. For example, the mask may be implanted underneath the cornea's epithelium sheet, beneath the cornea's Bowman membrane, in the top layer of the cornea's stroma, or in the cornea's stroma. When the mask is placed underneath the cornea's epithelium sheet, removal of the mask requires little more than removal of the cornea's epithelium sheet.

Figure 6A:
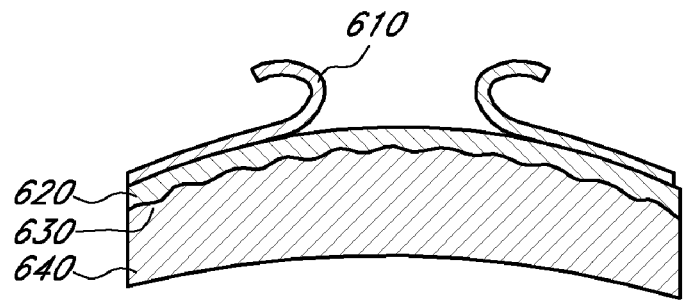
FIGS. 6a through 6c show a mask, configured to increase the depth of focus of the human eye, inserted underneath the cornea's epithelium sheet.
Figure 6B:
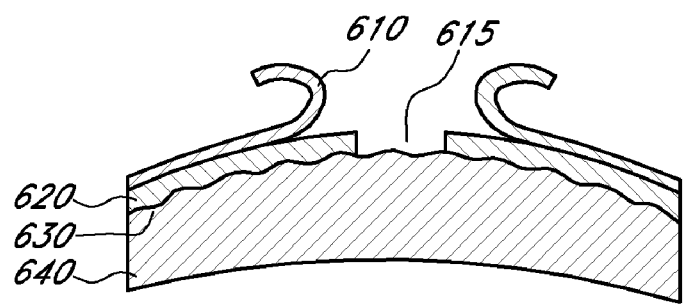
Figure 6C:
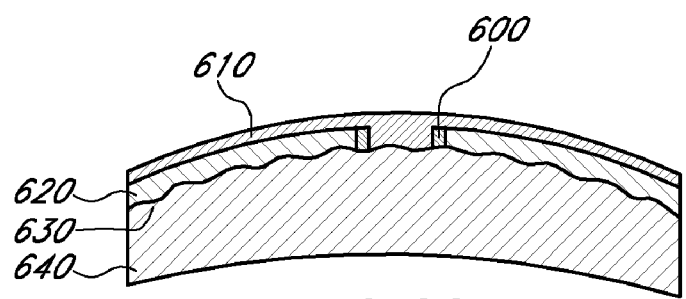

FIGS. 6a through 6c show mask 600 inserted underneath epithelium sheet 610. In this embodiment, the surgeon first removes epithelium sheet 610. For example, as shown in FIG. 6a, epithelium sheet 610 may be rolled back. Then, as shown in FIG. 6b, the surgeon creates depression 615 in Bowman's member 620. Depression 615 should be of sufficient depth and width to both expose top layer 630 of stroma 640 and to accommodate mask 600. Mask 600 is then placed in depression 615. Last, epithelium sheet 610 is placed over mask 600. Over time, as shown in FIG. 6c, epithelium sheet 610 will grow and adhere to top layer 630 of stroma 640, as well as mask 600 depending, of course, on the composition of mask 600. As needed, a contact lens may be placed over the incised cornea to protect the mask.

Figure 7A:
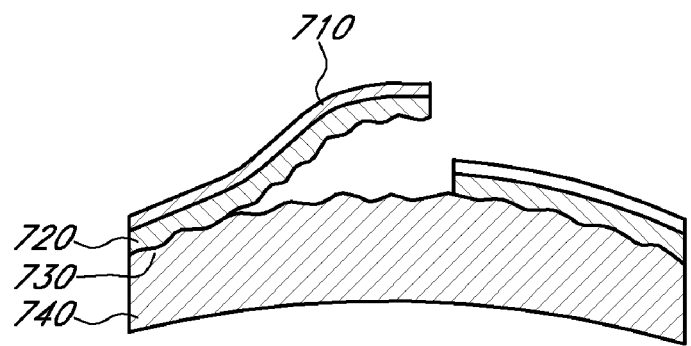
FIGS. 7a through 7c show a mask, configured to increase the depth of focus of the human eye, inserted beneath the cornea's Bowman's membrane.
Figure 7B:
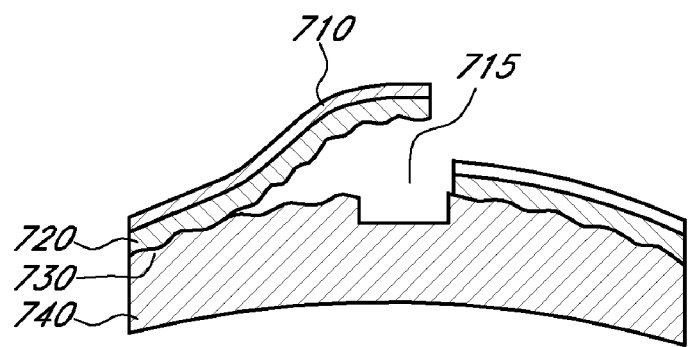
Figure 7C:
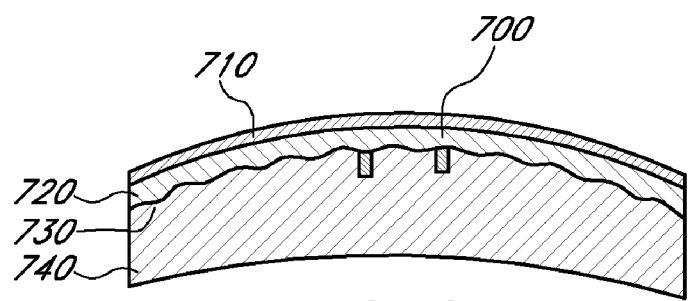

FIGS. 7a through 7c show mask 700 inserted beneath Bowman's membrane 720. In this embodiment, as shown in FIG. 7a, the surgeon first hinges open Bowman's member 720. Then, as shown in FIG. 7b, the surgeon creates depression 715 in top layer 730 of stroma 740. Depression 715 should be of sufficient depth and width to accommodate mask 700. Then, mask 700 is placed in depression 715. Last, Bowman's member 720 is placed over mask 700. Over time, as shown in FIG. 7c, epithelium sheet 710 will grow over the incised area of Bowman's member 720. As needed, a contact lens may be placed over the incised cornea to protect the mask.

In an alternate embodiment, a mask of sufficient thinness, i.e., less than substantially 20 microns, may be placed underneath epithelium sheet 610, or beneath Bowman's member 720, without creating a depression in the top layer of the stroma.

In an alternate method for surgically implanting a mask in the eye of a patient, the mask may be threaded into a channel created in the top layer of the stroma. In this method, a curved channeling tool creates a channel in the top layer of the stroma, the channel being in a plane parallel to the surface of the cornea. The channeling tool either pierces the surface of the cornea or, in the alternative, is inserted via a small superficial radial incision. In the alternative, a laser focusing an ablative beam may create the channel in the top layer of the stroma. In this embodiment, the mask may be a single segment with a break, or it may be two or more segments.

In another alternate method for surgically implanting a mask in the eye of a patient, the mask may be injected into the top layer of the stroma. In this embodiment, an injection tool with a stop penetrates the surface of the cornea to the specified depth. For example, the injection tool may be a ring of needles capable of producing a mask with a single injection. In the alternative, a channel may first be created in the top layer of the stroma. Then, the injector tool may inject the mask into the tunnel. In this embodiment, the mask may be a pigment, or it may be pieces of pigmented material suspended in a biocompatible medium. The pigment material may be made of a polymer or, in the alternative, made of a suture material.

In still another alternate method for surgically implanting a mask in the eye of a patient, the mask may be placed beneath the corneal flap created during keratectomy, when the outermost 20% of the cornea is hinged open.

In one still other alternate method for surgically implanting a mask in the eye of a patient, the mask may be placed in a pocket created in the cornea's stroma.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A method for implanting a mask in a cornea comprising an epithelial sheet, a Bowman's membrane, and a stroma, the stroma having a top layer, the method comprising:
   creating a flap in a portion of the cornea;
   creating a depression in the top layer of the stroma by completely removing a portion of the stroma from the cornea, the depression being of sufficient depth and width to accommodate a mask, the mask comprising a centrally located pinhole-like optical aperture and a structure surrounding the aperture, the structure further having varying degrees of opacity, each of the varying degrees of opacity preventing transmission of a substantial portion of visible light incident on the structure;
   placing the mask in the depression; and
   placing the flap over the mask,
   wherein the mask increases the depth of focus of the eye and a curvature of the cornea is not substantially changed after placing the mask.

2. The method of claim 1, wherein the mask is configured to produce light interference.

3. The method of claim 1, wherein the mask is configured to produce light scattering.

4. The method of claim 1, wherein the mask is configured to produce reflection.

5. The method of claim 1, wherein the mask is configured to block visual aberrations.

6. The method of claim 1, further comprising:
   placing a contact lens over at least a portion of the cornea until the epithelial sheet has grown over the hinged Bowman's membrane.

7. A method for implanting an ophthalmic device in a cornea comprising an epithelial sheet, a Bowman's membrane, and a stroma, the stroma having a top layer, the method comprising:
   creating a channel in the stroma by completely removing a portion of the stroma from the cornea, the channel being in a plane parallel to the cornea's surface; and
   placing an ophthalmic device in the channel, the ophthalmic device comprising a mask comprising a centrally located pinhole-like optical aperture and a structure surrounding the aperture, the structure further having varying degrees of opacity, each of the varying degrees of opacity preventing transmission of a substantial portion of visible light incident on the structure,
   wherein the mask increases the depth of focus of the eye and a curvature of the cornea is not substantially changed after implanting the mask.

8. The method of claim 7, wherein the mask is configured to produce light interference.

9. The method of claim 7, wherein the mask is configured to produce light scattering.

10. The method of claim 7, wherein the mask is configured to produce light reflection.

11. The method of claim 7, wherein the mask is configured to block visual aberrations.

12. The method of claim 7, further comprising threading the mask into the channel.

13. The method of claim 7, further comprising injecting the mask into the channel.

14. A method for implanting a mask in a cornea, the mask configured to increase the depth of focus of the human eye, the cornea comprising an epithelium sheet, the method comprising:
   forming a corneal flap, the corneal flap comprising substantially the outermost 20% of the cornea;
   placing a mask on a portion of the cornea exposed by the flap, the mask configured to provide an optical effect whereby the depth of focus of the human eye is increased, the mask comprising a centrally located pinhole-like optical aperture and a structure surrounding the aperture, the structure further having varying degrees of opacity, each of the varying degrees of opacity preventing transmission of a substantial portion of visible light incident on the structure; and
   placing the corneal flap over the mask,
   wherein a curvature of the cornea is not substantially changed after implanting the mask.

15. The method of claim 14, wherein the mask is configured to produce light interference.

16. The method of claim 14, wherein the mask is configured to produce light scattering.

17. The method of claim 14, wherein the mask is configured to produce light reflection.

18. The method of claim 14, wherein the mask is configured to block visual aberrations.

19. The method of claim 14, further comprising:
   placing a contact lens over a portion of the cornea until the epithelial sheet has grown over the hinged corneal flap.

20. A method for implanting an ophthalmic device in a cornea comprising a stroma, the method comprising:
   creating a pocket in the stroma, the pocket being of sufficient size to accommodate an ophthalmic device, the ophthalmic device comprising a mask configured to provide an optical effect whereby the depth of focus of the human eye is increased, the mask comprising a centrally located pinhole-like optical aperture and a structure surrounding the aperture, the structure further having varying degrees of opacity, each of the varying degrees of opacity preventing transmission of a substantial portion of visible light incident on the structure; and
   placing the ophthalmic device in the pocket,
   wherein a curvature of the cornea is not substantially changed after implanting the mask.

21. The method of claim 20, wherein the mask is configured to produce light interference.

22. The method of claim 20, wherein the mask is configured to produce light scattering.

23. The method of claim 20, wherein the mask is configured to produce light reflection.

24. The method of claim 20, wherein the mask is configured to block visual aberrations.

* * * * *